United States Patent
Öberg et al.

(10) Patent No.: US 10,828,316 B2
(45) Date of Patent: *Nov. 10, 2020

(54) METHOD OF TREATING BACTERIAL INFECTIONS

(71) Applicant: ULTUPHARMA AB, Uppsala (SE)

(72) Inventors: Bo Öberg, Uppsala (SE); Anders Broberg, Uppsala (SE); Bengt Guss, Uppsala (SE); Jolanta Levenfors, Orbyhus (SE); Joakim Bjerketorp, Uppsala (SE); Christina Nord, Uppsala (SE)

(73) Assignee: ULTUPHARMA AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/775,202

(22) PCT Filed: Jan. 27, 2017

(86) PCT No.: PCT/SE2017/050071
§ 371 (c)(1),
(2) Date: May 10, 2018

(87) PCT Pub. No.: WO2017/131576
PCT Pub. Date: Aug. 3, 2017

(65) Prior Publication Data
US 2018/0325934 A1    Nov. 15, 2018

(30) Foreign Application Priority Data
Jan. 27, 2016  (SE) ..................................... 1650097

(51) Int. Cl.
| | | |
|---|---|---|
| *A01N 43/04* | (2006.01) | |
| *A61K 31/70* | (2006.01) | |
| *A61K 31/7072* | (2006.01) | |
| *A61K 31/505* | (2006.01) | |
| *A61K 45/06* | (2006.01) | |
| *A61K 31/635* | (2006.01) | |
| *A61K 31/708* | (2006.01) | |
| *A61P 31/04* | (2006.01) | |
| *A61K 9/00* | (2006.01) | |
| *A61K 31/506* | (2006.01) | |

(52) U.S. Cl.
CPC ........ *A61K 31/7072* (2013.01); *A61K 9/0053* (2013.01); *A61K 31/505* (2013.01); *A61K 31/635* (2013.01); *A61K 31/708* (2013.01); *A61K 45/06* (2013.01); *A61P 31/04* (2018.01); *A61K 31/506* (2013.01); *A61K 2300/00* (2013.01); *Y02A 50/30* (2018.01)

(58) Field of Classification Search
None
See application file for complete search history.

(56) References Cited

FOREIGN PATENT DOCUMENTS

| WO | 2017192744 A1 | 11/2017 |
| WO | 2017192845 A1 | 11/2017 |

OTHER PUBLICATIONS

Oefner et al. Journal of Antimicrobial Chemotherapy (2009), vol. 63, pp. 687-698.*
Feola et al. Clinical and Vaccine Immunology (2006), vol. 13, pp. 193-201.*
Sommadossi et al. Antimicrobial Agents and Chemotherapy (1988), vol. 32, pp. 997-1001.*
Senthikumar et al. Clinical Infectious Diseases (2001), vol. 33, pp. 1412-1416.*
Zander, J. et al, "Synergistic Antimicrobial Activities of Folic Acid Antagonists and Nucleoside Analogs" Antimicrob. Agents Chemother., 2010, vol. 54, pp. 1226-1231.
Klubes, P. et al, "Use of Uridine Rescue to Enhance the Antitumor Selectivity of 5-Fluorouracil" Cancer Res., 1983, vol. 43, pp. 3182-3186.
Doleans-Jordheim, A. "Zidovudine (AZT) has a bactericidal effect on enterobacteria and induces genetic modifications in resistant strains" Eur. J. Clin. Microbial. Infect. Dis., 2011, vol. 30, pp. 1249-1256.
Jordheim, L. P., "Gemcitabine is active against clinical multiresistant *Staphylococcus aureus* strains and is synergistic with gentamicin" Int. J. Antimicrob. Agents, 2012, vol. 39, pp. 444-447.
Walker, U. A., "Uridine abrogates mitochondrial toxicity related to nucleoside analogue reverse transcriptase inhibitors in HepG2 cells" Antivir. Ther. 2003, vol. 8, pp. 463-470.
International Search Report cited in PCT/SE2017/050071, dated May 2, 2017, 5 pages.
"Iclaprim for the Treatment of Complicated Skin and Skin Structure Infections" FDA Briefing Document for Anti-Infective Drugs Advisory Committee Meeting, Nov. 20, 2008, 31 pages.
Bourne, "Utility of the Biosynthetic Folate pathway for Targets in Antimicrobial Discovery", Antibiotics, 2014, 3, 1-28.
Swedish Search Report cited in Patent Application No. 1850429-0, dated Sep. 26, 2019, 3 pages.

(Continued)

*Primary Examiner* — Patrick T Lewis
(74) *Attorney, Agent, or Firm* — Rothwell, Figg, Ernst & Manbeck, P.C.

(57) ABSTRACT

The present invention relates to a composition comprising a first compound which is a nucleoside analogue capable of inhibiting a bacterial colonisation or infection of a subject; a second compound which is capable of decreasing mitochondrial toxicity of said nucleoside analogue and surprisingly enhance the antibacterial effect of the combination; and a third compound capable of decreasing the concentration in bacteria of nucleosides and/or nucleotides known to compete with nucleoside analogues. The first compound may be AZT, FdUrd, 5-fluorouracil, BrdUrd, IdUrd, didanosine or gemcitabine; the second compound may be uridine or a uridine-comprising compound; and the third compound may be trimethoprim or a compound comprising trimethoprim, such as trimethoprim-sulfa.

24 Claims, No Drawings

(56) References Cited

OTHER PUBLICATIONS

Dirienzo et al: "Efficacy of Trimethoprim-Sulfamethoxazole for the Prevention of Bacterial Infections in a Randomized Prophylaxis Trial of Patients with Advanced HIV Infection", AIDS Research and Human Retroviruses., vol. 18, No. 2, Jan. 20, 2002, pp. 89-94.
Singh et al: "The Complex Mechanism of Antimycobacterial Action of 5-Fluorouracil", Chemistry and Biology., vol. 22, No. 1, Jan. 22, 2015, pp. 63-75.
Communication pursuant to Article 94(3) EPC issued in EP 17 744 649.9, dated May 11, 2020, 7 pages.

\* cited by examiner

METHOD OF TREATING BACTERIAL INFECTIONS

CROSS REFERENCE TO RELATED APPLICATION

This application is a 35 U.S.C. 371 National Phase Entry Application from PCT/SE2017/050071, filed Jan. 27, 2017, which claims the benefit of Patent Application No. SE 1650097-7 filed on Jan. 27, 2016 the disclosure of which is incorporated herein in its entirety by reference.

TECHNICAL FIELD

The present invention relates to an antibacterial composition the low toxicity of which allows using a known antiviral or anticancer drug in humans in higher concentrations than hitherto been possible. More specifically, the invention relates to a method of enhancing the antibacterial effect of known antiviral and/or anti-cancer drugs and at the same time increase safety; a novel pharmaceutical composition; and a method of treatment or prevention of bacterial infections using such a composition. Such combinations can be used to treat and prevent infections by bacteria resistant to present medications.

BACKGROUND ART

The dramatic increase in resistant bacteria, both Gram-negative and Gram-positive, has been identified by The World Health Organization as one of the three major threats to global health. The pipeline of new antibiotics is almost dry and during the past 15 years, only five novel antibacterial agents have been approved by the US FDA. The lack of interest in developing new treatments of bacterial infections has in the past decade been common to most 'Big Pharma'. Almost 30.000 patients are dying due to multidrug resistant bacteria every year both in the EU and the US, and the situation is even worse in other parts of the world. These alarming figures are going to increase before new treatments become available. The Infectious Diseases Society of America reported in 2010 that 10 antibiotics with new mechanisms of action were needed before 2020 (CID 2010: 50 (15 April) 2081-2083 The 10X'20 initiative). Predictions of annual mortality due to resistant bacteria in 2050 show tenfold increased figures for EU and US and close to 5 million in Asia (Review on Antimicrobial Resistance. Antimicrobial Resistance: Tackling a crisis for the Health and Wealth of Nations, 2014).

The evolutionary origin of mitochondria from bacteria, and their similarity, has been reviewed. The bacterial origin of mitochondria has the consequence that many nucleoside analogs, primarily designed as antiviral or anticancer drugs, can inhibit both bacteria and mitochondria. However, their dose-limiting toxicity in patients and animals at concentrations required to inhibit bacteria restricts their use as antibiotics.

More specifically, nucleoside analogs like AZT, FdUrd, didanosine, BrdUrd, IdUrd and gemcitabine are phosphorylated by both mitochondria and bacteria, and as triphosphates they inhibit DNA synthesis. These compounds also induce mutations in mitochondria, which can result in patients developing cardiomyopathy. Maintaining mitochondrial functional quality in cardiomyocytes is important.

In order to decrease mitochondrial toxicity in HIV-patients treated with AZT, some patients have additionally been given uridine (Sutinen et al, Antiviral Therapy, 2007, 12: 97-105). Adding uridine or cytidine has decreased toxicity in vitro, while not prevented the inhibition of HIV replication by AZT (Sommadossi et al, Antimicrob. Ag. Chemother. 1988, 32: 997-1001). Attempts in vitro to achieve a decrease in toxicity of AZT by adding thymidine was found to inhibit not only the antiviral effect on HIV but also to inhibit the antibacterial effect of AZT (Schepherd et al, J. Pharm. Pharmacol. 1992, 44:704-706) and increase toxicity (Sommadossi et al, 1988, Cox and Harmenberg, Antiviral Chem. Chemother., (1990): 269-277). Uridine has been reported to abrogate adverse effects of pyrimidine analogues (Walker et al Antiviral Therapy 2006, 11:25-34).

In cancer patients, the toxicity of 5-fluorouracil, related to FdUrd, has been decreased by the addition of uridine (Leyva et al Cancer Research, 1984, 44:5928-5932).

Uridine has an oral bioavailability of 7-8% and oral doses of 3×35 g/day (Nucleomax) gave a plasma Cmax of 35 µg/ml (Sutinen et al, 2007). Infusion of 1-12 g/sq. m. gave plasma levels of up to 250 µg/ml (Leyva et al, 1984). Uridine has a low toxicity and prodrugs with high bioavailability have been reported, such as triacetyluridine (Nucleomax) (Weinberg et al PLoS ONE 6(2): e14709) and can be used.

U.S. Pat. No. 6,992,072 (Walker) relates to the combatting of side-effects of nucleoside analogues capable of inhibiting reverse transcriptase, such as AZT. More specifically, pyrimidine nucleosides are administered to treat or avoid lipodystrophy resulting from such drugs. Combining AZT with sulfamethoxazole-trimethoprim in the treatment of *Pneumocystis* murina infection in mice showed adverse effects on the humoral immune response (Feola and Garvy, Clin. Vaccine Immunol. 2006, 13:193-201).

WO 2014/147405 (Hu) relates to a combination of AZT with polymyxin, a large polypeptide antibiotic commonly used against *Pseudomonas aueriginosa*, which combination exhibits a synergistic antimicrobial activity.

It has been found that the inhibitory concentration of nucleoside analogs against viral replication in vitro is highly dependent on concentrations of normal nucleosides (Larsson, Brannstrom and Öberg, Antimicrob. Ag. Chemother. 1983, 24: 819-822). In vitro data of antiviral effect underestimates the concentration required in vivo due to the presence of competing nucleosides/nucleotides in various tissues (Böttiger and Öberg, Current Opin. Anti-Inf. Drugs, 2000, 2: 255-264).

The presence of up to 30 µM (7 µg/ml) thymidine in skin explains why the in vitro highly potent anti-herpes drug acyclovir needs to be present in high concentration in skin to inhibit cutaneous herpes virus replication (Harmenberg, Intervirology, 1983, 20:48-51, Harmenberg et al, FEBS Letters, 1985, 188: 219-2219). Thymidine concentrations in various human tissues range between 0.5 and 20 µg/g tissue (Valentino et al, FEBS Letters, 2007, 581:3410-3414) and can be expected to influence the concentration of a nucleoside analog, such as AZT, required to inhibit bacteria. Higher concentrations of a pyrimidine analog can be required in vivo than predicted from in vitro assays of antibacterial effect performed in the absence of thymidine.

Zander et al (Johannes Zander, Silke Besier, Hanns Ackermann, and Thomas A. Wichelhaus in Antimicrobial Agents and Chemotherapy, March 2010, p.1226-1231: "Synergistic Antimicrobial Activities of Folic Acid Antagonists and Nucleoside Analogiues") performed a screening for nucleoside analogs that impair bacterial thymidine utilization and analyzed the combined antimicrobial activities of nucleoside analogs and folic acid antagonists in the presence of thymidine. It was found that 5-iodo-2'-deoxyuridine enhanced the antibacterial effect against *S. aureus* of trimethoprim-sulfmethoxazole (SXT) in the presence of thymidine, but that thymidine decreases the antibacterial effect.

Doléans-Jordheim et al (A. Doléans-Jordheim, R. Bergeron, F. Bereyziat, S. Ben-Larbi, O. Dumitrescu, M.-A. Mazoyer, F. Morfin, C. Dumontet, J. Freney, L. P. Jordheim in Eur J Clin Microbiol Infect Dis (2011) 30:1249-1256: "Zidovudine (AZT) has a bactericidal effect on enterobacteria and induces genetic modifications in resistant strains") describe AZT (zidovudine) as having a potential antibacterial activity specifically against enterobacteria, but according to the MIC results of Doléans-Jordheim et al, AZT had no effect on Gram-positive bacteria. An additive or synergistic activity was observed when AZT was administered together with two aminoglycoside antibiotics, namely amikacin and gentamicin. According to Doléans-Jordheim et al, their results indicate that the synergy of AZT with such antibiotics could indicate a supplemental use in clinical infectiology that could prevent the appearance of resistance. However Doléans-Jordheim et al do not discuss the cytotoxicity of AZT in detail, it is simply noted that with regard to side effects, AZT is quite well tolerated when used in an anti-HIV setting, and that the total duration of treatment should be much shorter for bacterial infections.

Jordheim et al (Lars Petter Jordheim, Sabrina Ben Larbi, Olivier Fendrich, Claire Ducrot, Emanuelle Bergeron, Charles Dumontet, Jean Freney, Anne Doléans-Jordheim in International Journal of Antimicrobial Agents 39 (2012) 444-447: "Gemcitabine is active against clinical multiresistant *Staphylococcus aureus* strains and is synergistic with gentamicin") provides a specific study of the antibacterial activity of the nucleoside analogue gemcitabine against *Staphylococcus aureus* strains such as MSSA, MRSA and GISA. In order to reduce the toxicity of gemcitabine to human cells, and potentially also to reduce the risk of bacterial resistance, Jordheim et al suggest the testing of nucleosides specifically phosphorylated by bacterial kinases.

Klubes et al (Philip Klubes and Ingeborg Cerna in Cancer Research 43, 3182-3186, July 1983): "Use of Uridine Rescue to enhance the Antitumor Selectivity of 5-Fluorouracil") relates to the delayed infusion of uridine to increase the selectivity of antitumor effect (cytotoxic) of fluorinated pyrimidines such as FUra. Further, the specificity of uridine to rescue mice from the lethal toxicity thereof was also studied. More specifically, the effects of Fura was studied and compared in tumor cells and normal tissue, respectively. Klubes et al show that uridine rescue increased the therapeutic index of certain melanome, but not in leukemia. Thus, as the reasons for this difference is not clear, Klubes et al cannot be applied to other conditions.

SUMMARY OF INVENTION

In general, the invention relates to the surprising finding that compounds decreasing the mitochondrial toxicity of nucleoside analogs will not decrease their antibacterial effect, and that the antibacterial effect can even be enhanced by such compounds. This is surprising since mitochondria have a bacterial origin and one should expect similar metabolic effects of added compounds to bacteria and to mitochondria. The invention relates to compounds such as AZT, FdUrd, BrdUrd, IdUrd, 5-fluorouracil, didanosine or gemcitabine, or their prodrugs, which increase or at least retain their antibacterial effects by the addition of compounds such as uridine, which at the same time decrease the harmful mitochondrial toxicity and to the addition of a third treatment component, such as trimethoprim or other inhibitors of tetrahydrofolate synthesis, which in bacteria, but not in mitochondria, decrease the concentration of nucleosides/nucleotides competing with nucleoside analogs such as AZT. The enhanced antibacterial effect of adding uridine to AZT combined with trimethoprim has not previously been reported. These new triple combinations give synergistic antibacterial effects, and will allow therapeutically effective doses with enhanced safety and without limiting toxicity in human patients and animals. The invention provides concentrations of the combinations which are safe and high enough to overcome the problem with competing nucleosides, such as thymidine, which can be high in tissues where bacteria should be eliminated. These combinations have the ability to inhibit bacteria resistant to present therapies as these are likely to act by other mechanisms.

A first aspect of the invention is a method of enhancing the antibacterial effect in a subject of a nucleoside analogue such as AZT, FdUrd, 5-fluorouracil, BrdUrd, IdUrd, didanosine and gemcitabine, which method comprises administering an effective amount of the nucleoside analogue to a subject in need thereof in combination with a second compound selected from the group consisting of uridine and uridine-comprising compounds and a third compound selected from the group consisting of trimethoprim and trimethoprim such as trimethoprim-sulfa. In all of the herein described aspects and embodiments, the use of prodrug(s) of any one of the three different components to enhance oral bioavailability or make iv formulations less prone to give local irritation is encompassed within the scope of the invention.

A second aspect of the invention is a composition comprising at least one first compound which is a nucleoside analogue capable of inhibiting a bacterial colonisation or infection of a subject; at least one second compound capable of decreasing mitochondrial toxicity of said nucleoside analogue and surprisingly enhance the antibacterial effect of the first compound; and at least one third compound capable of decreasing the concentration in bacteria of nucleosides and/or nucleotides known to compete with nucleoside analogues and thereby decrease their antibacterial effect.

A specific aspect of the invention is a pharmaceutical preparation comprising at least one first compound selected from the group consisting of AZT, FdUrd, 5-fluorouracil, BrdUrd, IdUrd, didanosine and gemcitabine; at least one second compound selected from the group consisting of uridine and uridine-comprising compounds; and at least one third compound selected from the group consisting of trimethoprim and trimethoprim compounds, such as trimethoprim-sulfa, together with a pharmaceutically acceptable carrier.

A third aspect of the invention is a method of treating or preventing a bacterial infection or colonisation in a subject, which method comprises administering an effective dose of a first compound selected from the group consisting of AZT, FdUrd, 5-fluorouracil, BrdUrd, IdUrd, didanosine and gemcitabine; and at least one second compound selected from the group consisting of uridine and uridine-comprising compounds and at least one third compound selected from the group consisting of trimethoprim and trimethoprim compounds, such as trimethoprim-sulfa or compounds inhibiting synthesis of tetrahydrofolate.

Further embodiments, advantages and other details of the invention will appear from the description of the invention, as defined by the appended claims.

DEFINITIONS

The term "nucleoside analogue" relates herein to a substance, structurally related to a nucleoside and capable of inhibiting nucleic acid metabolism.

The term "AZT" relates herein to the nucleoside analogue azidothymidine, also known as zidovudine i.e. 3'-azido-3'-deoxythymidine.

The term "therapeutically effective amount" as used herein refers to an amount sufficient to inhibit or at least to substantially decrease bacterial growth associated with a bacterial infection or colonisation.

The term "toxicity" of a composition as used herein refers herein to the undesired damage caused to a subject receiving treatment. Thus, for example, the toxicity of an antibacterial compound or composition does not include the effect caused the bacteria but to the effect on otherwise healthy cells. Consequently, the term "mitochondrial toxicity" refers herein to the harmful and normally undesired effect on the mitochondria of the recipient of treatment.

The terms "treatment" or "treating" as used herein refer to the full or partial removal of the symptoms and signs of the condition as well as any trace or sign of the causing bacteria.

The term "subject" means herein a recipient of a treatment or administration scheme according to the invention. Thus, a "subject" is for example a human in need of antibacterial treatment, such as a human patient.

Unless otherwise indicated, all technical and scientific terms used herein have the same meanings as commonly understood by one of ordinary skill in the art to which this invention belongs.

DETAILED DESCRIPTION OF THE INVENTION

As appears from the above, a combination of AZT and uridine has been found not only to retain the broad antibacterial effect of AZT against multidrug resistant bacteria, but uridine also enhanced the antibacterial effect of AZT, while at the same time uridine reduces toxicity to animal cells. AZT+uridine are combined with trimethoprim, or compounds with similar effects, as shown in the experimental part below, to achieve a synergistic antibacterial effect, while retaining a decreased toxicity.

In a first aspect, the invention relates to a method of enhancing an antibacterial effect in a subject of a nucleoside analogue commonly used against viral infections and/or in cancer treatment, as discussed above, while at the same time reducing toxicity.

More specifically, one embodiment of the invention is a method of enhancing the antibacterial effect in a subject of a nucleoside analogue, which method comprises administering an effective amount of at least one nucleoside analogue to a subject in need thereof in combination with at least one second compound selected from the group consisting of uridine and uridine-comprising compounds; and at least one third compound selected from the group consisting of trimethoprim and/or other trimethoprim compounds. In this context, it is to be understood that the term "trimethoprim compounds" includes trimethoprim-comprising compounds as well as prodrugs capable of giving rise to trimethoprim or such compounds. The term "trimethoprim-comprising compounds" is understood herein to mean any compound which comprises a sufficient amount of trimethoprim to provide an equivalent or close to equivalent effect to methoprim in the herein described method and use.

The second compound may be a compound known to reduce the toxicity of a nucleoside analogue, such as uridine and/or uridine-comprising compounds. In this context, the term "uridine-comprising compounds" is understood to mean any compound which comprises a sufficient amount of uridine to provide an equivalent or close to equivalent effect to uridine in the herein described method and use. As will appear from the Experimental part below, such as in Table 9A, according to the present invention, the second compound will also enhance the antibacterial effect of a nucleoside analogue, which has presently been used to treat viral infections or cancer.

Nucleoside analogues commonly used as drugs and used according to the invention may be one or more compound selected from the group consisting of AZT, FdUrd, gemcitabine, didanosine, 5-fluorouracil, 5-bromouracil, 5-iodouracil, FLT, flucytosine, 5-bromouridine, stavudine, telbivudine, entecavir, emtricitabine, adefovir, lamivudine, tenofovir, vidarabine, abacavir, cytarabine, aracytidine, cidofovir, zalcitabine, ribavirin, idoxuridine, trifluoruridine, mercaptopurine, 5-ethyldeoxyuridine, thioguanine, 5-chlorodeoxyuridine, pentostatin, cladribine, clofarabine, fludarabine, nalarabine, allopurinol, FMdc, sinefungin, troxacitabine, vidaza, nelarabine, decitabine, CNDAC, ECyd, sofosbuvir, sapacitabine and mericitabine. As the skilled person will appreciate, prodrugs of such compounds may also be useful according to the invention to improve oral bioavailability and/or penetration and/or uptake into bacteria.

In one embodiment, the nucleoside analogue is selected from the group consisting of AZT, FdUrd, 5-fluorouracil, BrdUrd, IdUrd, didanosine and gemcitabine.

The compound comprising trimethoprim may e.g. be trimethoprim-sulfa. As the skilled person will appreciate, other trimethoprim-containing compounds may be useful provided the advantageous effect of enhancing the antibacterial effect is obtained.

In an advantageous embodiment of the method according to the invention, the combined antibacterial effect of the nucleoside analogue and the second and third compound is greater than the sum of the effect provided if administered separately. In other words, a synergistic effect has been observed, as will be illustrated by the Experimental part below.

In a specific embodiment of the first aspect, the nucleoside analogue is AZT, the second compound is uridine and the third compound is trimethoprim.

The subject may be a human or an animal, as will be discussed in more detail below, and the antibacterial effect may be directed towards a bacterial infection caused by Gram-negative and/or Gram-positive bacteria, especially by bacteria which have acquired resistance to antibiotics in present use.

In a second aspect, the invention relates to a composition comprising as a first compound at least one nucleoside analogue capable of inhibiting a bacterial colonisation or infection of a subject; at least one second compound capable of decreasing mitochondrial toxicity of said nucleoside analogue and increasing the antibacterial effect; and at least one third compound capable of decreasing the concentration in bacteria of nucleosides and/or nucleotides known to compete with nucleoside analogues.

The first compound may be one or more of the nucleoside analogues commonly used as drugs, as discussed above in relation to the first aspect of the invention. In one embodiment, the first compound is selected from the group consisting of AZT, FdUrd, BrdUrd, IdUrd, didanosine and gemcitabine.

The second compound may be a compound as discussed above in relation to the first aspect of the invention, such as a compound commonly known to reduce the toxicity and surprisingly increase the antibacterial effect of the first compound, and hence allow larger doses, of nucleoside analogue-based drugs. In one embodiment of the composition, the second compound is uridine.

The third compound may be a compound as discussed above in relation to the first aspect of the invention, such as a folate analogue, such as trimethoprim, or a compound comprising trimethoprim such as trimethoprim-sulfa, any other trimethoprim compound, or a compound inhibiting bacterial synthesis of tetrahydrofolate. In one embodiment, the third compound is trimethoprim and/or other trimethoprim compound(s).

The compound according to the invention is the first medical use of a composition comprising at least the herein defined three components. Thus, the present invention relates to a composition according to the invention for use as a medicament.

Further, as appears from the present application as a whole, the present composition comprising at least the herein defined three components is suggested for the first time as an antibacterial composition. Thus, the present invention also relates to a composition according to the invention for use in the treatment or prevention of bacterial infections. It will appear from the Experimental part below which bacteria the present composition is advantageously used against, and the skilled person in this area is well aware of which diseases and/or conditions they may cause.

A specific aspect of the invention is a composition according to the invention which is a pharmaceutical preparation. Such a pharmaceutical preparation comprises at least one first compound selected from the group consisting of AZT, FdUrd, 5-fluorouracil, BrdUrd, IdUrd, didanosine and gemcitabine; at least one second compound selected from the group consisting of uridine and uridine-comprising compounds; and at least one third compound selected from the group consisting of trimethoprim and trimethoprim compounds, such as trimethoprim-sulfa, together with a pharmaceutically acceptable carrier.

The present invention also encompasses any pharmaceutically acceptable salt of the above, wherein the biological effectiveness and properties of the compounds of the present disclosure are retained.

Further, the pharmaceutical composition of the invention may comprise an excipient selected from the group comprising, but not limited to, binders and compression aids, coatings and films, colouring agents diluents and vehicles disintegrants, emulsifying and solubilising agents, flavours and sweeteners, repellents, glidants and lubricants, plasticisers, preservatives, propellants, solvents, stabilisers, suspending agents and viscosity enhancers.

The pharmaceutical composition of the invention may be administered in a variety of unit dosages depending on the method of administration, target site, physiological state of the subject, and other medicaments administered.

As the skilled person will appreciate, in severely sick patients, intravenous dosing with fixed combinations is preferred, and the compositions of the invention may alternatively be formulated for delivery by injection. As an example, the compound is delivered by injection by any one of the following routes: intravenous, intramuscular, intradermal, intraperitoneal or subcutaneous route.

Thus, in one embodiment, the compositions described are liquid formulations, such as liquids suitable for intravenous administration. The skilled person will be capable of preparing such formulations based on the common general knowledge of the field and assisted by common textbooks and publications in the area.

Examples of liquid compositions include solutions, emulsions, injection solutions, and solutions contained in capsules. Generally, any solvent that has the desired effect and can be administered to a subject may be used. The solvent may be a pure solvent or may be a mixture of liquid solvent components. In some variations the solution formed is an in situ gelling formulation. Solvents and types of solutions that may be used are well known to those versed in drug delivery technologies.

The composition described herein may be in the form of a liquid suspension. The liquid suspensions may be prepared according to standard procedures known in the art. Examples of liquid suspensions include micro-emulsions, the formation of complexing compounds, and stabilising suspensions. The liquid suspension may be in diluted or concentrated form. Liquid suspensions for oral use may contain suitable preservatives, antioxidants, and other excipients known in the art functioning as one or more of dispersion agents, suspending agents, thickening agents, emulsifying agents, wetting agents, solubilising agents, stabilising agents, flavouring and sweetening agents, colouring agents, and the like. The liquid suspension may contain glycerol and water.

For less severely sick patients, or for preventive purposes, the composition according to the invention may advantageously be administered orally, such as in solid dosage forms such as powder, tablets, pills, and capsules, or in liquid dosage forms, such as oral pastes, elixirs, syrups, solutions and suspensions.

Thus, in one embodiment, the pharmaceutical composition of the invention may be formulated for oral administration. Traditional inactive ingredients may be added to provide desirable colour, taste, stability, buffering capacity, dispersion, or other known desirable features. Conventional diluents may be used to make compressed tablets. Both tablets and capsules may be manufactured as sustained-release compositions for the continual release of medication over a period of time. Compressed tablets may be in the form of sugar coated or film coated tablets, or enteric-coated tablets for selective disintegration in the gastrointestinal tract. Liquid dosage forms for oral administration may contain colouring and/or flavouring to increase patient compliance.

Dosing can be done by giving compounds such as AZT, FdUrd, 5-fluorouracil, BrdUrd, IdUrd, didanosine or gemcitabine combined in one separate formulation with compounds such as trimethoprim, trimethoprim-sulfa and/or other trimethoprim compounds and uridine and/or uridine-comprising compounds in one or more separate formulation(s).

As appears from the above, the invention also encompasses the use of a compound according to the invention, or therapeutically acceptable salts thereof, in the manufacture of medicaments for the treatment of a bacterial colonisation or infection in a subject.

With regard to general doses and forms of administration the compounds used in the present invention, reference is made e.g. to Gahart's 2016, $32^{nd}$ Edition: "Intravenous medications, A Handbook for Nurses and Health Professionals (Elsevier.com).

The present invention also includes a method of inhibiting a bacterial colonisation or infection of a host, which method includes contacting the bacteria with an effective amount of an antibacterial nucleoside analogue in combination with uridine or a uridine-comprising compound and an effective amount of at least one trimethoprim compound, wherein the concentration of nucleosides and/or nucleotides competing with the nucleoside analogue in bacteria or parasites is reduced while mitochondria in the colonised or infected area of said host remains substantially uneffected.

Examples of compounds decreasing nucleoside/nucleotide levels in bacteria but not in mitochondria are didox, trimidox, metronidazole, rifampicin, trimethoprim, sulfa, sulfonamides, gemcitabine, FMdC, clofarabine, methotrexate, mercaptopurine, para-amino-salicylic acid, inhibitors of bacterial ribonucleotide reductase and prodrugs of such compounds to improve oral bioavailability and/or penetration/uptake into bacteria. In one embodiment, uridine is co-administered with the nucleoside analogue and trimethoprim or a compound comprising trimethoprim, such as trimethoprim-sulfa.

In one embodiment, the antibacterial nucleoside analogue is selected from the group consisting of AZT; FdUrd; 5-flurouracil, BrdUrd, IdUrd, didanosine and gemcitabine.

In a third aspect, the invention relates to a method of treating or preventing a bacterial infection or colonisation in a subject, which method comprises administering to said subject an effective dose of at least one first compound selected from the group consisting of AZT, FdUrd, 5-fluorouracil, BrdUrd, IdUrd, didanosine and gemcitabine; at least one second compound selected from the group consisting of uridine and uridine-comprising compounds; and a third compound selected from the group consisting of trimethoprim and trimethoprim compounds.

All details, discussions and examples of the first, second and third compounds provided above in the context of the first and the second aspect of the invention will also apply to the third aspect.

The skilled person in this field will be aware of commonly used doses of the compounds used in combination according to the invention, and will therefore be capable of prescribing the appropriate doses and/or amounts used for a given context.

Thus, the method according to the invention may include daily infusion of AZT as the first compound at a dose of 1.5-15 mg/kg; daily infusion of uridine as the second compound at a dose of 30-300 mg/kg; and as a third compound trimethoprim at a dose of 1.5-15 mg/kg. Such treatment may include 4-6 doses daily of each compound.

Further, the method according to the invention may include daily oral administration of AZT as the first compound at a dose of 2-20 mg/kg and daily oral administration of uridine as the second compound at a dose of 60-600 mg/kg and as the third compound trimethoprim at a dose of 2-20 mg/kg. Such treatment may include 1-4 daily doses.

If AZT or other nucleosides are given as prodrugs, such as 5"-O-aminoacid derivatives, an enhanced antibacterial effect can be achieved or a reduced dose given.

Further illustrative doses will be presented in the Experimental part below, and the skilled person will be able to design suitable dose schemes and regimes based on this specification as a whole together with common general knowledge.

The bacteria may be Gram-negative and/or Gram-positive bacteria, which bacteria may or may not be anaerobic, such as *Acinetobacter; Bacillus; Bordetella; Campylobacter; Cit-robacter; Clostridium; Corynebacteria; Enterobacter; Escherichia; Haemophilus; Heliobacter; Klebsiella; Legionella; Listeria; Micrococcus; Moraxella; Mycobacteria; Neisseria; Proteus; Pseudomonas; Salmonella; Shigella; Staphylococcus; Streptococcus; Vibrio* and *Yersinia*. Some relevant bacteria will be further illustrated in the Experimental part below, where publically available strains have been tested, as marked or noted e.g. by reference to the relevant depository such as ATCC.

The subject receiving treatment in accordance with the present invention may be any subject capable of colonisation and infection by bacteria, as appears from below.

EXPERIMENTAL PART

The examples below are provided for illustrative purposes only, and should not be construed as limiting the invention as defined by the appended claims. All references provided below or elsewhere in the present application are hereby included herein via reference. The present invention makes use of, unless otherwise indicated, conventional microbiological techniques within the skill of the art. Such conventional techniques are known to the skilled worker.

Example 1: Bacterial Strains Tested

Table 1 below shows some of the bacterial strains used in studies to test the antibacterial effect.

TABLE 1

| Pathogen | Denotation | Working code no | Properties |
|---|---|---|---|
| *Escherichia coli* (S) | CCUG 24T | 1 | Type strain |
| *Escherichia coli* (R) | LMG 15862 | 2 | Penicillin resistant strain |
| *Acinetobacter baumannii* (S) | LMG 1041T | 3 | Type strain |
| *Escherichia coli* (S) | LMG 8223 | 5 | |
| *Enterobacter cloacae* (S) | LMG 2783T | 6 | Type strain |
| *Klebsiella pneumoniae* (S) | CCUG 225T | 7 | Type strain |
| *Klebsiella pneumoniae* (R) | LMG20218 | 8 | ESBL |
| *Pseudomonas aeruginosa* (S) | LMG 6395 | 10 | |
| *Staphylococcus aureus* (S/R) | LMG 10147 | 12 | MSSA/weak penicillinase producer |
| *Staphylococcus aureus* (R) | LMG 15975 | 13 | MRSA |

(S)—Strains sensitive to antibiotics;
(R)—Strains resistant to antibiotics
BCCM/LMG—strains obtained from Belgian Coordinated Collection of Microorganisms
CCUG—strains obtained from Culture Collection of University of Göteborg Example 2: Antibacterial Effect of AZT Combined with Uridine Examples of the antibacterial effect of the combination AZT and uridine against bacteria are given in Table 2 below. More specifically, the Minimal Inhibitory Concentration (MIC, μg/ml) of AZT against a range of human pathogens in the presence of varying concentrations of uridine is provided.

TABLE 2

| | Uridine concentration (μg/ml) | | | | | |
|---|---|---|---|---|---|---|
| Bacterial pathogen | 0 | 1 | 10 | 50 | 100 | 200 |
| *E. coli* strain no 2 | >20 ≤ 25 | >20 ≤2 5 | >20 ≤ 25 | >15 ≤ 20 | >5 ≤ 15 | >5 ≤ 15 |
| *E. coli* strain no 1 | >0.5 ≤ 1 | nt | >0.5 ≤ 1 | >0.5 ≤ 1 | >0.5 ≤ 1 | >0.5 ≤ 1 |

TABLE 2-continued

| Bacterial pathogen | Uridine concentration (μg/ml) | | | | | |
|---|---|---|---|---|---|---|
| | 0 | 1 | 10 | 50 | 100 | 200 |
| E. coli strain no 5 | >4 ≤ 8 | nt | nt | nt | nt | nt |
| K. pneumoniae strain no 8 | >15 ≤ 25 | >10 ≤20 | >10 ≤ 20 | >10 ≤ 20 | >10 ≤ 20 | >10 ≤ 20 |
| K. pneumoniae strain no 7 | >1 ≤ 2 | nt | nt | nt | nt | nt |
| E. cloacae strain no 6 | >10 ≤ 20 | nt | >5 ≤ 10 | >5 ≤ 10 | >2 ≤ 5 | >2 ≤ 5 |
| A. baumannii strain no 3 | >150 | nt | >150 | >150 | >150 | >150 |
| P. aeruginosa strain no 10 | >150 | nt | >150 | >150 | >150 | >150 |
| S. aureus strain no 13 | >150 | nt | >150 | >150 | >150 | >150 |

AZT was active against *E. coli*, *K. pneumonia* and *E. cloacae*. Addition of up to 200 μg/ml of uridine surprisingly resulted in an increase in antibacterial effect, in contrast to the previously reported decrease in antibacterial effect by addition of thymidine.

Example 3: Synergistic Effect of AZT Combined with Uridine and Trimethoprim

In order to further increase the antibacterial effect of AZT, or other nucleoside analogs including prodrugs, trimethoprim, trimethoprim+sulfa, or other compounds decreasing the concentration of nucleosides/nucleotides in bacteria, but not in mitochondria, can be added. The result from testing a penicillin resistant *E. coli* (strain 2 in Table 1) is shown in Table 3 below. More specifically, the Minimal Inhibitory Concentration (MIC, μg/ml) of AZT against *E. coli* strain no 2 in the presence of varying concentrations of uridine and respectively 2, 1 and 0.5 μg/ml of trimethoprim is provided.

TABLE 3

| Trimethoprim concentration | Uridine concentration (μg/ml) | | | | |
|---|---|---|---|---|---|
| (μg/ml) | 0 | 1 | 10 | 100 | 200 |
| 0 | >20 ≤ 25 | >10 ≤ 20 | >10 ≤ 20 | >2 ≤ 10 | >2 ≤ 10 |
| 2 | >0.006 ≤ 0.012 | ≤0.006 | ≤0.006 | >0.012 ≤ 0.025 | >0.006 ≤ 0.012 |
| 1 | >0.012 ≤ 0.025 | ≤0.006 | ≤0.006 | >0.025 ≤ 0.05 | >0.012 ≤ 0.025 |
| 0.5 | >0.012 ≤ 0.025 | ≤0.006 | >0.05 ≤ 0.1 | >0.025 ≤ 0.05 | >0.012 ≤ 0.025 |

MIC of trimethoprim only against *E. coli* strain no 2 was established to be >8 ≤ 16 μg/ml A surprisingly strong synergistic effect against *E. coli* was observed for this combination according to the invention, and the presence of uridine will also reduce toxicity in patients.

Example 4: Synergistic Effect of AZT Combined with Uridine and Trimethoprim

A further example is given in Table 4 below, which shows the synergistic effects against *E. cloacae* (strain 6 in Table 1) of combinations of AZT with trimethoprim and uridine. More specifically, the Minimal Inhibitory Concentration (MIC, μg/ml) of AZT against *E. cloacae* in the presence of varying concentrations of uridine and respectively 2 and 1 μg/ml of trimethoprim is provided.

TABLE 4

| Trimethoprim concentration | Uridine concentration (μg/ml) | | | |
|---|---|---|---|---|
| (μg/ml) | 0 | 10 | 100 | 200 |
| 0 | >10 ≤ 20 | >5 ≤ 10 | >2 ≤ 5 | >2 ≤ 5 |
| 2 | >0 ≤ 0.05 | >0 ≤ 0.05 | >0 ≤ 0.05 | nt |
| 1 | >0 ≤ 0.05 | >0 ≤ 0.05 | >0 ≤ 0.05 | nt |

MIC of trimethoprim only against *E. cloacae* strain no 6 was established to be >16 ≤ 32 μg/ml

Example 5: Further Bacteria Tested for AZT Combined with Uridine and Trimethoprim Table 5 below shows further bacterial strains tested for sensitivity to AZT with trimethoprim and uridine when used in a fixed ratio of concentrations.

TABLE 5

| Pathogen | Denotation | Properties |
|---|---|---|
| Serratia marescens | EN0454 | |
| Micrococcus luteus | EN0455 | |
| Proteus mirabilis | EN0457 | |
| Escherichia coli B | EN0458 | |
| Pseudomonas aeruginosa | EN0459 | |
| Pseudomonas aeruginosa | EN0460 | |
| Enterobacter aerogenes | EN0461 | |
| Klebsiella pneumoniae | EN0463 | |
| Staphylococcus epidermidis | EN0456 | |
| Citrobacter sp. | EN0465 | |
| Salmonella typhimurium | EN0466 | |
| Acinetobacter pittii or nosocomialis | EN0180 | |
| Klebsiella oxytoca | EN0392 | |
| Pseudomonas aeruginosa | EN0422 | |
| Proteus mirabilis ST19 | EN0445 | |
| Escherichia coli | EN001 | WT |

TABLE 5-continued

| Pathogen | Denotation | Properties |
|---|---|---|
| Escherichia coli | EN002 | DtolC (isogenic to ATCC 25922) |
| Escherichia coli | EN003 | D22 (lps mutant, hypersensitive) |
| Pseudomonas aeruginosa | EN004 | WT |
| Pseudomonas aeruginosa | EN005 | Efflux-defective (isogenic to PAO1) |
| Klebsiella pneumoniae | EN006 | WT |
| Acinetobacter baumannii | EN007 | WT |
| Staphylococcus aureus | EN008 | Gram-positive control |
| Klebsiella pneumoniae | EN0010 | WT |
| Klebsiella pneumoniae | EN0011 | Efflux mutant |
| Escherichia coli | EN0012 | WT |
| Escherichia coli | EN0013 | DtolC delition efflux mutant |
| Pseudomonas aeruginosa | EN0014 | WT |
| Pseudomonas aeruginosa | EN0015 | Efflux mutant |
| Acinetobacter baumannii | EN0016 | WT |
| Acinetobacter baumannii | EN0017 | Efflux mutant |

Example 6: Strong Antibacterial Effects in Further Bacteria Tested

The antibacterial effect (MIC, μg/ml) of the combination of AZT, trimethoprim and uridine on the broad range of Gram-negative and Gram-positive bacterial pathogens and on selected mutant strains of Table 5 is shown in Table 6 below. Efflux mutations in *K. pneumoniae, P. aeruginosa* and *A. baumanii* were found to increase the sensitivity.

TABLE 6

| Bacterial pathogen | Substance concentration needed for total inhibition of pathogen growth (μg/ml) | | |
|---|---|---|---|
| | AZT | Trimethoprim | Uridine |
| S. marescens EN0454 | 1 | 1 | 250 |
| M. luteus EN0455 | 2 | 2 | 500 |
| P. mirabilis EN0457 | 2 | 2 | 500 |
| E. coli B EN0458 | <0.008 | <0.008 | <2 |
| P. aeruginosa EN0459 | >4 | >4 | >1000 |
| P. aeruginosa EN0460 | >4 | >4 | >1000 |
| E. aerogenes EN0461 | 0.25 | 0.25 | 60 |
| K. pneumoniae EN0463 | 0.06 | 0.06 | 16 |
| S. epidermidis EN0456 | 0.06 | 0.06 | 16 |
| Citrobacter sp. EN0465 | >4 | >4 | >1000 |
| S. typhimurium EN0466 | 0.06 | 0.06 | 16 |
| A. pittii or A. nosocomialis EN0180 | >4 | >4 | >1000 |
| K. oxytoca EN0392 | 0.06 | 0.06 | 16 |
| P. aeruginosa EN0422 | >4 | >4 | >1000 |
| P. mirabilis ST19 EN0445 | >4 | >4 | >1000 |
| E. coli EN001 | 0.06 | 0.06 | 16 |
| E. coli EN002 | 0.016 | 0.016 | 4 |
| E. coli EN003 | <0.008 | <0.008 | <2 |
| P. aeruginosa EN004 | >4 | >4 | >1000 |
| P. aeruginosa EN005 | 1 | 1 | 250 |
| K. pneumoniae EN006 | 0.06 | 0.06 | 16 |
| A. baumannii EN007 | >4 | >4 | >1000 |
| S. aureus EN008 | 1 | 1 | 250 |
| K. pneumoniae EN010 | 0.5 | 0.5 | 125 |
| K. pneumoniae EN011 | 0.125 | 0.125 | 30 |
| E. coli EN012 | <0.008 | <0.008 | <2 |
| E. coli EN013 | <0.008 | <0.008 | <2 |
| P. aeruginosa EN014 | >4 | >4 | >1000 |
| P. aeruginosa EN015 | 2 | 2 | 500 |
| A. baumannii EN016 | >4 | >4 | >1000 |
| A. baumannii EN017 | 1 | 1 | 250 |

The doses of AZT, uridine and trimethoprim can be given to patients to give steady state peak plasma levels of 0.1-10 μg/ml of AZT, 0.5-5 μg/ml of trimethoprim and 20-250 μg/ml of uridine.

Example 7: FdUrd as the Antibacterial Nucleoside Analogue Shows Synergistic Effect Against *E. cloacae* and *S. aureus* when Combined with Uridine and Trimethoprim Table 7A below shows the Minimal Inhibitory concentration (MIC, μg/ml) of FdUrd against *E. cloacae* strain 6 in the presence of varying concentrations of uridine and 2 and 1 μg/ml of trimethoprim, respectively.

TABLE 7A

| | MIC FdUrd (μg/ml) | |
|---|---|---|
| Trimethoprim (μg/ml) | Uridine 0 (μg/ml) | Uridine 10 (μg/ml) |
| Trimethoprim only | >4 ≤ 8 | N/A |
| 2 | >1 ≤ 2.5 | >0.05 ≤ 0.1 |
| 1 | >2.5 | >2.5 |
| 0 | >30 | >30 |

MIC of trimethoprim only against *E. coli* strain no 2 was established to be >8 ≤ 16 μg/ml Table 7B below shows the minimal Inhibitory concentration (MIC, μg/ml) of FdUrd applied in combination with varying concentrations of trimethoprim against *S. aureus* strain 13 without and in the presence of uridine.

TABLE 7B

| | MIC FdUrd (μg/ml) | | | |
|---|---|---|---|---|
| Uridine (μg/ml) | Trimetho-prim 0.25 (μg/ml) | Trimetho-prim 0.5 (μg/ml) | Trimetho-prim 1 (μg/ml) | Trimetho-prim 2 (μg/ml) |
| 0 | >5 ≤ 10 | >1 ≤ 5 | >1 ≤ 5 | >1 ≤ 5 |
| 10 | >1 ≤ 5 | >1 ≤ 5 | >1 ≤ 5 | >0.1 ≤ 1 |
| 100 | >1 ≤ 5 | >1 ≤ 5 | >0.05 ≤ 0.1 | >0.05 ≤ 0.1 |

The addition of uridine will decrease toxicity of FdUrd in patients but not decrease the antibacterial effect and trimethoprim gives a synergistic antibacterial effect. The steady state peak level of FdUrd can be 0.2-2 μg/ml in patients of trimethoprim 0.5-5 μg/ml and of uridine 20-250 μg/ml.

Example 8: Potent Antibacterial Effects of FdUrd with Trimethoprim and Uridine Against Several Gram Negative and Gram Positive Bacteria Table 8 below shows the antibacterial effect (MIC, μg/ml) of the combination of FdUrd, trimethoprim and uridine on the broad range of Gram-negative and Gram-positive bacterial pathogens and on selected mutant strains (Table 5).

TABLE 8

| Bacterial pathogen | Substance concentration needed for total inhibition of pathogen growth (μg/ml) | | |
|---|---|---|---|
| | FdUrd | Trimethoprim | Uridine |
| S. marescens EN0454 | >4 | >8 | >400 |
| M. luteus EN0455 | 2 | 4 | 200 |
| P. mirabilis EN0457 | 1 | 2 | 100 |

TABLE 8-continued

| Bacterial pathogen | Substance concentration needed for total inhibition of pathogen growth (µg/ml) | | |
|---|---|---|---|
| | FdUrd | Trimethoprim | Uridine |
| E. coli B EN0458 | 0.032 | 0.064 | 3 |
| P. aeruginosa EN0459 | >4 | >8 | >400 |
| P. aeruginosa EN0460 | >4 | >8 | >400 |
| E. aerogenes EN0461 | 1 | 2 | 100 |
| K. pneumoniae EN0463 | 0.25 | 0.5 | 25 |
| S. epidermidis EN0456 | <0.008 | <0.016 | <0.8 |
| Citrobacter sp. EN0465 | >4 | >8 | >400 |
| S. typhimurium EN0466 | 0.125 | 0.25 | 13 |
| A. pittii or A. nosocomialis EN0180 | 4 | 8 | 400 |
| K. oxytoca EN0392 | 0.125 | 0.25 | 13 |
| P. aeruginosa EN0422 | >4 | >8 | >400 |
| P. mirabilis ST19 EN0445 | 0.5 | 1 | 50 |
| E. coli EN001 | 0.125 | 0.25 | 13 |
| E. coli EN002 | 0.032 | 0.064 | 6 |
| E. coli EN003 | 0.016 | 0.032 | 1.6 |
| P. aeruginosa EN004 | >4 | >8 | >400 |
| P. aeruginosa EN005 | 0.25 | 0.5 | 25 |
| K. pneumoniae EN006 | 0.5 | 1 | 50 |
| A. baumannii EN007 | >4 | >8 | >400 |
| S. aureus EN008 | <0.008 | <0.016 | <0.8 |
| K. pneumoniae EN010 | 0.5 | 1 | 50 |
| K. pneumoniae EN011 | 0.064 | 0.125 | 6 |
| E. coli EN012 | 0.032 | 0.064 | 3 |
| E. coli EN013 | 0.016 | 0.032 | 1.6 |
| P. aeruginosa EN014 | >4 | >8 | >400 |
| P. aeruginosa EN015 | 1 | 2 | 100 |
| A. baumannii EN016 | 4 | 8 | 400 |
| A. baumannii EN017 | 0.5 | 1 | 50 |

Example 9: Didanosine as the Antibacterial Nucleoside Analogue Shows Synergistic Effect Against E. coli when Combined with Uridine and Trimethoprim Table 9A below shows a potent effect against E. coli when combining didanosine and trimethoprim and uridine. Steady state peak plasma levels of didanosine can be 1-5 µg/ml in patients, of trimethoprim 0.5-5 µg/ml and of uridine 20-250 µg/ml. More specifically, Table 9A provides the Minimal inhibitory concentration (MIC, µg/ml) of didanosine against E. coli strain 2 in the presence of varying concentrations of uridine and 2 and 1 µg/ml of trimethoprim, respectively.

TABLE 9A

| Trimethoprim (µg/ml) | MIC Didanosine (µg/ml) | | |
|---|---|---|---|
| | Uridine 0 (µg/ml) | Uridine 10 (µg/ml) | Uridine 100 (µg/ml) |
| Trimethoprim only | >8 ≤ 16 | N/A | N/A |
| 2 | >2.5 | >2.5 | >0.1 ≤ 0.05 |
| 1 | >2.5 | >2.5 | >0.1 ≤ 0.05 |
| 0 | >30 | >30 | >30 |

Table 9B shows the inhibition of E. cloacae by combining didanosine, trimethoprim and uridine. More specifically, the Minimal Inhibitory Concentration (MIC, µg/ml) of didanosine against E. cloacae strain 6 in the presence of varying concentrations of uridine and 2 and 1 µg/ml of trimethoprim, respectively, is provided.

TABLE 9B

| Trimethoprim (µg/ml) | MIC Didanosine (µg/ml) | |
|---|---|---|
| | Uridine 0 (µg/ml) | Uridine 10 (µg/ml) |
| 2 | >2.5 | >2.5 |
| 1 | >1 ≤ 2.5 | >0.1 ≤ 0.5 |
| 0 | >30 | >30 |

MIC of trimethoprim only against E. cloacae strain 6 was established to be >16 ≤ 32 µg/ml.

Example 10: Potent Antibacterial Effects of Didanosine with Trimethoprim and Uridine Against Several Gram-Negative and Gram-Positive Bacteria Table 10 shows the antibacterial effect (MIC, µg/ml) of the combination of didanosine, trimethoprim and uridine on a broad range of Gram-negative and Gram-positive bacterial pathogens and on selected mutant strains (Table 5).

| Bacterial pathogen | Substance concentration needed for total inhibition of pathogen growth (µg/ml) | | |
|---|---|---|---|
| | Didanosine | Trimethoprim | Uridine |
| S. marescens EN0454 | >4 | >8 | >400 |
| M. luteus EN0455 | 2 | 4 | 200 |
| P. mirabilis EN0457 | 2 | 4 | 200 |
| E. coli B EN0458 | 0.032 | 0.064 | 3 |
| P. aeruginosa EN0459 | >4 | >8 | >400 |
| P. aeruginosa EN0460 | >4 | >8 | >400 |
| E. aerogenes EN0461 | 0.5 | 1 | 50 |
| K. pneumoniae EN0463 | 0.25 | 0.5 | 25 |
| S. epidermidis EN0456 | 0.064 | 0.125 | 6 |
| Citrobacter sp. EN0465 | >4 | >8 | >400 |
| S. typhimurium EN0466 | 0.25 | 0.5 | 25 |
| A. pittii or A. nosocomialis EN0180 | >4 | >8 | >400 |
| K. oxytoca EN0392 | 0.25 | 0.5 | 25 |
| P. aeruginosa EN0422 | >4 | >8 | >400 |
| P. mirabilis ST19 EN0445 | 1 | 2 | 100 |
| E. coli EN001 | 0.125 | 0.25 | 13 |
| E. coli EN002 | 0.032 | 0.064 | 6 |
| E. coli EN003 | 0.032 | 0.064 | 6 |
| P. aeruginosa EN004 | >4 | >8 | >400 |
| P. aeruginosa EN005 | 0.5 | 1 | 50 |
| K. pneumoniae EN006 | 0.5 | 1 | 50 |
| A. baumannii EN007 | >4 | >8 | >400 |
| S. aureus EN008 | 0.5 | 1 | 50 |
| K. pneumoniae EN010 | 0.5 | 1 | 50 |
| K. pneumoniae EN011 | 0.125 | 0.25 | 13 |
| E. coli EN012 | 0.064 | 0.125 | 6 |
| E. coli EN013 | 0.016 | 0.032 | 1.6 |
| P. aeruginosa EN014 | >4 | >8 | >400 |
| P. aeruginosa EN015 | 1 | 2 | 100 |
| A. baumannii EN016 | >4 | >8 | >400 |
| A. baumannii EN017 | 1 | 2 | 100 |

Example 11: Influence of Uridine on the Effect of BrdUrd and Trimethoprim

Table 11 below shows the MIC (µg/ml) of BrdU applied in combination with 2 µg/ml of trimethoprim without and with the presence of uridine against isolates of E. coli strain 2 and S. aureus strain 13.

TABLE 11

| | MIC BrdUrd (µg/ml) Pathogen | |
|---|---|---|
| Uridine (µg/ml) | E. coli strain 2 | S. aureus strain 13 |
| 0 | >16 ≤ 32 | >4 ≤ 8 |
| 10 | >8 ≤ 16 | ≤2 |
| 100 | >4 ≤ 8 | ≤2 |

MIC (µg/ml) of trimethoprim only were established to be respectively >16 ≤ 32 µg/ml (E. coli strain 2) and <32 (S. aureus strain 13).

Example 12: Influence of Thymidine on Antibacterial Effects

The presence of thymidine in various tissues and in plasma under various disease conditions has to be taken into account when dosing AZT with trimethoprim and uridine, and similar combinations.

Table 12 A and B shows the influence of thymidine on inhibition of E. coli and E. cloacae by AZT with trimethoprim and uridine at high thymidine concentrations Plasma and tissue concentrations of thymidine in humans have been reported to be in the range of 0.1 to 20 uM (0.025-5 µg/ml).

More specifically, Table 12 shows the Minimal Inhibitory Concentration (MIC, µg/ml) of AZT against: (A) E. coli strain 2 and (B) E. cloacae strain 6 in the presence of respectively thymidine only, thymidine and 100 µg/ml uridine as well as thymidine, 100 µg/ml uridine and 1 µg/ml trimethoprim.

TABLE 12

| Thymidine (µM) | MIC AZT (µg/ml) Uridine (U) and Trimethoprim (T) (µg/ml) | | |
|---|---|---|---|
| | 0 (U) | 100 (U) | 100 (U) and 1 (T) |
| A | | | |
| 30 | >30 | >30 | >0.5 |
| 10 | >30 | >30 | >0.1 ≤ 0.5 |
| 0 | >20 ≤ 30 | >5 ≤ 10 | >0.05 ≤ 0.01 |
| B | | | |
| 30 | >5 ≤ 10 | >10 | >0.1 |
| 10 | >5 ≤ 10 | >5 ≤ 10 | >0.05 ≤ 0.1 |
| 0 | >5 ≤ 10 | >2.5 ≤ 5 | ≤0.001 |

Example 13: Enhanced Antibacterial Effect of AZT Plus Trimethoprim by Addition of Uridine in the Presence of Thymidine Table 13 below shows MIC values (ug/ml) of respectively AZT, trimethoprim and AZT+trimethoprim mixed in proportions of 1:1 in the presence of 5 uM thymidine and added 0, 10, and 100 ug/ml of uridine against A) E. coli strain 2 and B) E. cloacae strain 6.

TABLE 13

| | MIC (µg/ml) | | |
|---|---|---|---|
| Uridine (µg/ml) | AZT | Trimethoprim | AZT + Trimethoprim (1:1) |
| A | | | |
| 0 | >30 | >5 ≤ 10 | >1.2 ≤ 2.5 |
| 10 | >25 ≤ 30 | >2.5 ≤ 5 | >0.3 ≤ 0.6 |
| 100 | >10 ≤ 20 | >2.5 ≤ 5 | >0.15 ≤ 0.3 |

TABLE 13-continued

| | MIC (µg/ml) | | |
|---|---|---|---|
| Uridine (µg/ml) | AZT | Trimethoprim | AZT + Trimethoprim (1:1) |
| B | | | |
| 0 | >5 ≤ 10 | <20 | >0.04 ≤ 0.075 |
| 10 | >2.5 ≤ 5 | <20 | ≤0.04 |
| 100 | >2.5 ≤ 5 | <20 | ≤0.04 |

Example 14: Enhanced Effect of AZT Plus Trimethoprim by Addition of Uridine in the Presence of Thymidine Table 14 shows the effect of uridine alone and uridine in the presence of 10 µM thymidine on MIC (µg/ml) of AZT/Trimethoprim combination mixed in proportions of 1:1 against A) E. coli strain 2; B) E. coli strain 6; and C) K. pneumoniae strain 8.

TABLE 14

| | MIC AZT/Trimethoprim (1:1) (µg/ml) Thymidine µM | |
|---|---|---|
| Uridine (µg/ml) | 0 | 10 |
| A | | |
| 0 | >0.3 ≤ 0.6 | >0.6 ≤ 1.2 |
| 10 | >0.3 ≤ 0.6 | >0.6 ≤ 1.2 |
| 100 | >0.15 ≤ 0.3 | >0.3 ≤ 0.6 |
| B | | |
| 0 | >0.04 ≤ 0.08 | >0.15 ≤ 0.3 |
| 10 | >0.04 ≤ 0.08 | >0.15 ≤ 0.3 |
| 100 | >0.02 ≤ 0.04 | >0.08 ≤ 0.15 |
| C | | |
| 0 | >0.08 ≤ 0.15 | >0.15 ≤ 0.3 |
| 10 | >0.08 ≤ 0.15 | >0.08 ≤ 0.15 |
| 100 | >0.04 ≤ 0.08 | >0.08 ≤ 0.15 |

Example 15: Enhanced Effect of Uridine Alone and Uridine in the Presence of Thymidine The effect is shown of uridine alone and uridine in the presence of 10 µM thymidine on MIC (µg/ml) on an FdUrd/Trimethoprim combination mixed in proportions of 1:2 against A) E. coli strain 2; B) E. coli strain 6; C) K. pneumoniae strain 8, and D) S. aureus strain 13.

TABLE 15

| | MIC FdUrd/Trimethoprim (1:2) (µg/ml) Thymidine µM | |
|---|---|---|
| Uridine (µg/ml) | 0 | 10 |
| A | | |
| 0 | >10 ≤ 20/20 ≤ 40 | >10 ≤ 20/20 ≤ 40 |
| 10 | >10 ≤ 20/20 ≤ 40 | >20/>40 |
| 100 | >2.5 ≤ 5/5 ≤ 10 | >20/>40 |
| B | | |
| 0 | >0.3 ≤ 0.6/0.6 ≤ 1.2 | >0.3 ≤ 0.6/0.6 ≤ 1.2 |
| 10 | >0.3 ≤ 0.6/0.6 ≤ 1.2 | >0.3 ≤ 0.6/0.6 ≤ 1.2 |
| 100 | >0.3 ≤ 0.6/0.6 ≤ 1.2 | >0.3 ≤ 0.6/0.6 ≤ 1.2 |

TABLE 15-continued

| Uridine (µg/ml) | MIC FdUrd/Trimethoprim (1:2) (µg/ml) Thymidine µM | |
|---|---|---|
| | 0 | 10 |
| | C | |
| 0 | >1.2 ≤ 2.5/2.5 ≤ 5 | 2.5 ≤ 5/>5 ≤ 10 |
| 10 | >0.6 ≤ 1.2/>1.2 ≤ 2.5 | >0.6 ≤ 1.2/>1.2 ≤ 2.5 |
| 100 | >0.6 ≤ 1.2/>1.2 ≤ 2.5 | >0.6 ≤ 1.2/>1.2 ≤ 2.5 |
| | D | |
| 0 | >5 ≤ 10/10 ≤ 20 | 10 ≤ 20/>20 ≤ 40 |
| 10 | >2.5 ≤ 5/>5 ≤ 10 | 10 ≤ 20/>20 ≤ 40 |
| 100 | >0.6 ≤ 1.2/>1.2 ≤ 2.5 | >5 ≤ 10/10 ≤ 20 |

Example 16: Effect of Thymidine on the Inhibition by the Combination AZT with Trimethoprim and Uridine on a Panel of Gram-Negative and Gram-Positive Bacteria Table 16 below shows the antibacterial effect (MIC, µg/ml) of the combination of AZT, trimethoprim and uridine only in comparison to the effect of the same combination mixed with thymidine on a broad range of Gram-negative and Gram-positive bacterial pathogens (described in Table 5).

| | Substance concentration needed for total inhibition of pathogen growth µg/ml | | | | | | |
|---|---|---|---|---|---|---|---|
| | Combination 1 | | | Combination 2 | | | |
| Bacterial pathogen | AZT | Trimethoprim | Uridine | AZT | Trimethoprim | Uridine | Thymidine (µM) |
| S. marescens EN0454 | >4 | >4 | >400 | >4 | >4 | >400 | >120 |
| M. luteus EN0455 | 2 | 2 | 200 | >4 | >4 | >400 | >120 |
| P. mirabilis EN0457 | 2 | 2 | 200 | >4 | >4 | >400 | >120 |
| E. coli B EN0458 | <0.008 | <0.008 | <0.8 | <0.008 | <0.008 | <0.8 | <0.2 |
| P. aeruginosa EN0459 | >4 | >4 | >400 | >4 | >4 | >400 | >120 |
| P. aeruginosa EN0460 | >4 | >4 | >400 | >4 | >4 | >400 | >120 |
| E. aerogenes EN0461 | 0.25 | 0.25 | 25 | 2 | 2 | 200 | 60 |
| K. pneumoniae EN0463 | 0.125 | 0.125 | 12.5 | 0.25 | 0.25 | 25 | 8 |
| S. epidermidis EN0456 | 0.064 | 0.064 | 66.4 | 2 | 2 | 200 | 60 |
| Citrobacter sp. EN0465 | >4 | >4 | >400 | >4 | >4 | >400 | >120 |
| S. typhimurium EN0466 | 0.064 | 0.064 | 6.4 | 0.5 | 0.5 | 50 | 15 |
| A. pittii or A. nosocomialis EN0180 | >4 | >4 | >400 | >4 | >4 | >400 | >120 |
| K. oxytoca EN0392 | 0.064 | 0.064 | 6.4 | 0.5 | 0.5 | 50 | 15 |
| P. aeruginosa EN0422 | >4 | >8 | >400 | >4 | >4 | >400 | >120 |
| P. mirabilis ST19 EN0445 | 1 | 1 | 100 | >4 | >4 | >400 | >120 |
| E. coli EN001 | 0.064 | 0.064 | 6.4 | 1 | 1 | 100 | 30 |
| E. coli EN002 | 0.016 | 0.016 | 1.6 | 0.125 | 0.125 | 12.5 | 4 |
| E. coli EN003 | <0.008 | <0.008 | <0.8 | <0.008 | <0.008 | <0.8 | <0.2 |
| P. aeruginosa EN004 | >4 | >4 | >400 | >4 | >4 | >400 | >120 |
| P. aeruginosa EN005 | 0.5 | 0.5 | 50 | 1 | 1 | 100 | 30 |
| K. pneumoniae EN006 | 0.125 | 0.125 | 12.5 | 0.5 | 0.5 | 50 | 15 |
| A. baumannii EN007 | >4 | >4 | >400 | >4 | >4 | >400 | >120 |
| S. aureus EN008 | 1 | 1 | 100 | >4 | >4 | >400 | >120 |
| K. pneumoniae EN010 | 0.25 | 0.25 | 25 | 1 | 1 | 100 | 30 |
| K. pneumoniae EN011 | 0.032 | 0.032 | 3.2 | 0.25 | 0.25 | 25 | 8 |
| E. coli EN012 | <0.008 | <0.008 | <0.8 | <0.008 | <0.008 | <0.8 | <0.2 |
| E. coli EN013 | <0.008 | <0.008 | <0.8 | <0.008 | <0.008 | <0.8 | <0.2 |
| P. aeruginosa EN014 | >4 | >4 | >400 | >4 | >4 | >400 | >120 |
| P. aeruginosa EN015 | 2 | 2 | 200 | 2 | 2 | 200 | 60 |
| A. baumannii EN016 | >4 | >4 | >400 | >4 | >4 | >400 | >120 |
| A. baumannii EN017 | 1 | 1 | 100 | 1 | 1 | 100 | 30 |

Example 17: Effect of AZT Combined with Trimethoprim and Uridine on Multiresistant Bacteria Table 17A shows the E. coli and K. pneumoniae strains used and their genotypes and resistance patterns. The resistance pattern means that the strains are clinically resistant to the antibiotics listed.

TABLE 17A

| Pathogen | Denotation | Genotype | Resistance pattern |
|---|---|---|---|
| E. coli | EN0001 | ATCC 25922, WT | Wild type, control strain |
| E. coli | EN0134 | AmpC (CMY-4) | ESC, SXT |
| E. coli | EN0135 | ESBL (SHV-2a) | ESC (I), GEN, TET |
| E. coli | EN0136 | ESBL (CTX-M-2) | ESC, GEN, AMK, SXT |
| E. coli | EN0137 | ESBL (CTX-M-15) | ESC, CIP, GEN, SXT |
| E. coli | EN0138 | ESBL (CTX-M-9) | ESC, CIP, SXT, TET, CML |

TABLE 17A-continued

| Pathogen | Denotation | Genotype | Resistance pattern |
|---|---|---|---|
| E. coli | EN0139 | ESBL (CTX-M-15) | ESC, CIP, AMK (I), SXT, TET |
| E. coli | EN0235 | MG1655 gyrA S83L D87N | CIP |
| K. pneumoniae | EN0006 | ATCC 13883 WT | Wild type, control strain |
| K. pneumoniae | EN0140 | AmpC (DHA-1); OmpK36 loss | ESC, CARBA, CIP, GEN + AMK, SXT, CML |
| K. pneumoniae | EN0233 | ST (CC/CG) = 11(258) | |
| K. pneumoniae | EN0142 | CHDL (OXA-48); ESBL (CTX-M-15) | ESC, ERT, CIP, GEN + TOB, SXT |
| K. pneumoniae | EN0143 | ESBL (SHV-12) | ESC, CIP, AMK (I), TOB, SXT |
| K. pneumoniae | EN0144 | MBL (VIM-1); ESBL (SHV-5); AmpC (CMY) | ESC, CARBA, CIP, GEN, AMK, SXT, TET |
| K. pneumoniae | EN0145 | KPC (KPC-2) | ESC, CARBA, CIP, AMK (I) |
| K. pneumoniae | EN0244 | | colistinR |
| K. pneumoniae | EN0245 | | colistinR |
| K. pneumoniae | EN0249 | | colistinR |
| K. pneumoniae | EN0262 | ESBL (+) -> (NP.+, MBL−, KPC+, CTX-M−, TEM+, OXA-1+) | |
| K. pneumoniae | EN0401 | | Carbapenemase + ESBL |
| K. pneumoniae | EN0436 | | colistinR |
| K. pneumoniae | EN0437 | DHA (+), CTX-M-1 | colistinR |
| P. aeruginosa | EN0004 | WT | Wild type, control strain |
| A. baumanii | EN0007 | WT | Wild type, control strain |

The combination of AZT with trimethoprim and uridine was tested against E. coli and K. pneumoniae with resistance to several antibiotics. The combination treatment has surprisingly potent effects against these resistant strains, including strains resistant to trimethoprim-sulfamethoxazole.

Table 17B shows the antibacterial effect (MIC, µg/ml) of the combination of AZT, trimethoprim and uridine against a range of E. coli and K. pneumoniae strains with resistance to commercial antibiotics.

| | Substance concentration needed for total inhibition of pathogen growth (µg/ml) | | |
|---|---|---|---|
| Bacterial pathogen | AZT | Trimethoprim | Uridine |
| E. coli EN0001 | 0.125 | 0.125 | 13 |
| E. coli EN0134 | 1 | 1 | 100 |
| E. coli EN0135 | 0.125 | 0.125 | 13 |
| E. coli EN0136 | 0.125 | 0.125 | 13 |
| E. coli EN0137 | 1 | 1 | 100 |
| E. coli EN0138 | 0.016 | 0.016 | 1.6 |
| E. coli EN0139 | 1 | 1 | 100 |
| E. coli EN0235 | <0.008 | <0.008 | <0.8 |
| K. pneumoniae EN0006 | 0.25 | 0.25 | 25 |
| K. pneumoniae EN0140 | 1 | 1 | 100 |
| K. pneumoniae EN0233 | 0.25 | 0.25 | 25 |
| K. pneumoniae EN0142 | 0.125 | 0.125 | 13 |
| K. pneumoniae EN0143 | >4 | >4 | >400 |
| K. pneumoniae EN0144 | 1 | 1 | 100 |
| K. pneumoniae EN0145 | 2 | 2 | 200 |
| K. pneumoniae EN0244 | 0.5 | 0.5 | 50 |
| K. pneumoniae EN0245 | 1 | 1 | 100 |
| K. pneumoniae EN0249 | 1 | 1 | 100 |
| K. pneumoniae EN0262 | 0.5 | 0.5 | 50 |
| K. pneumoniae EN0401 | >4 | >8 | >400 |
| K. pneumoniae EN0436 | 0.125 | 0.125 | 13 |
| K. pneumoniae EN0437 | >4 | >4 | >400 |
| P. aeruginosa EN0004 | >4 | >4 | >400 |
| A. baumannii EN0007 | >4 | >4 | >400 |

Example 18: MIC Values for One of the Least Sensitive Strains of K. pneumoniae Table 18 shows a comparison of MIC values for one of the least sensitive strains, K. pneumoniae EB0262. It is evident that the combination according to the invention is more potent than the 17 antibiotics listed, and that the inhibitory concentration can be used in patients.

Table 18 shows the MIC values of AZT, trimethoprim and uridine combination against K. pneumoniae EN0262 (resistance pattern ESBL (+)->(NP. +, MBL −, KPC+, CTX-M −, TEM +, OXA-1 +) in comparison to MIC values of several commercial antibiotics.

TABLE 18

| Antibiotic | MIC (µg/ml) |
|---|---|
| AZT; Trimethoprim; Uridine combination | 0.5; 0.5; 50 |
| AMP, ampicillin | >128 |
| AMC, amoxicillin-claculanic acid | >64 |
| PIP, piperacillin | >256 |
| TZP, piperacillin-tazobactam | 64 |
| CTX, cefotaxime | >32 |
| CAZ, ceftazidime | >32 |
| FEP, perfloxacin | >16 |
| ATM, aztreonam | >16 |
| IPM, imipenem | >4 |
| MEM, meropenem | >8 |
| GEN, gentamicin | 1 |
| AMK, amikacin | 8 |
| CIP, ciprofloxacin | >2 |
| SXT, trimethoprim-sulfamethoxazole | 4 |
| TET, tetracycline | 4 |
| TGC, tigecycline | 2 |
| CST, colistin | 1 |

MIC data for commercial antibiotics against K. pneumoniae EN0262 (resistance pattern ESBL (+) -> (NP.+, MBL−, KPC+, CTX-M−, TEM+, OXA-1+) were provided by IMBIM, BMC, Uppsala University.

Example 19: Effects of the Combination FdUrd, Trimethoprim and Uridine on Bacteria with Resistance to Commercial Antibiotics Table 19 shows the antibacterial effect (MIC, µg/ml) of the combination of FdUrd, trimethoprim and uridine against a range of E. coli and K. pneumoniae strains with resistance to commercial antibiotics.

| | Substance concentration needed for total inhibition of pathogen growth (µg/ml) | | |
|---|---|---|---|
| Bacterial pathogen | FdUrd | Trimethoprim | Uridine |
| E. coli EN0001 | 0.25 | 0.5 | 25 |
| E. coli EN0134 | >4 | >8 | >400 |

| Bacterial pathogen | FdUrd | Trimethoprim | Uridine |
|---|---|---|---|
| E. coli EN0135 | 0.25 | 0.5 | 25 |
| E. coli EN0136 | 1 | 2 | 100 |
| E. coli EN0137 | >4 | >8 | >400 |
| E. coli EN0138 | 0.25 | 0.5 | 25 |
| E. coli EN0139 | 0.5 | 1 | 50 |
| E. coli EN0235 | 0.06 | 0.125 | 6 |
| K. pneumoniae EN0006 | 0.5 | 1 | 50 |
| K. pneumoniae EN0140 | >4 | >8 | >400 |
| K. pneumoniae EN0233 | 0.5 | 1 | 50 |
| K. pneumoniae EN0142 | 0.125 | 0.125 | 13 |
| K. pneumoniae EN0143 | >4 | >8 | >400 |
| K. pneumoniae EN0144 | >4 | >8 | >400 |
| K. pneumoniae EN0145 | >4 | >8 | >400 |
| K. pneumoniae EN0244 | >4 | >8 | >400 |
| K. pneumoniae EN0245 | >4 | >8 | >400 |
| K. pneumoniae EN0249 | >4 | >8 | >400 |
| K. pneumoniae EN0262 | 2 | 4 | 200 |
| K. pneumoniae EN0401 | >4 | >8 | >400 |
| K. pneumoniae EN0436 | 0.25 | 0.5 | 25 |
| K. pneumoniae EN0437 | >4 | >8 | >400 |
| P. aeruginosa EN0004 | >4 | >8 | >400 |
| A. baumannii EN0007 | >4 | >8 | >400 |

Substance concentration needed for total inhibition of pathogen growth (μg/ml)

Example 20: Effects of the Combination Didanosine, Trimethoprim and Uridine on Bacteria with Resistance to Commercial Antibiotics Table 20 shows the antibacterial effect (MIC, μg/ml) of the combination of didanosine, trimethoprim and uridine against a range of E. coli and K. pneumoniae strains with resistance to commercial antibiotics.

| Bacterial pathogen | Didanosine | Trimethoprim | Uridine |
|---|---|---|---|
| E. coli EN0001 | 0.25 | 0.5 | 25 |
| E. coli EN0134 | >4 | >8 | >400 |
| E. coli EN0135 | 0.25 | 0.5 | 25 |
| E. coli EN0136 | >4 | >8 | >400 |
| E. coli EN0137 | >4 | >8 | >400 |
| E. coli EN0138 | 0.25 | 0.5 | 25 |
| E. coli EN0139 | 0.5 | 1 | 50 |
| E. coli EN0235 | 0.125 | 0.25 | 13 |
| K. pneumoniae EN0006 | 0.5 | 1 | 50 |
| K. pneumoniae EN0140 | >4 | >8 | >400 |
| K. pneumoniae EN0233 | 1 | 2 | 100 |
| K. pneumoniae EN0142 | >4 | >8 | >400 |
| K. pneumoniae EN0143 | >4 | >8 | >400 |
| K. pneumoniae EN0144 | >4 | >8 | >400 |
| K. pneumoniae EN0145 | >4 | >8 | >400 |
| K. pneumoniae EN0244 | >4 | >8 | >400 |
| K. pneumoniae EN0245 | >4 | >8 | >400 |
| K. pneumoniae EN0249 | >4 | >8 | >400 |
| K. pneumoniae EN0262 | 2 | 4 | 200 |
| K. pneumoniae EN0401 | >4 | >8 | >400 |
| K. pneumoniae EN0436 | 0.25 | 0.5 | 25 |
| K. pneumoniae EN0437 | >4 | >8 | >400 |
| P. aeruginosa EN0004 | >4 | >8 | >400 |
| A. baumannii EN0007 | >4 | >8 | >400 |

Substance concentration needed for total inhibition of pathogen growth (μg/ml)

Example 21: MIC Values of FdUrd, Trimethoprim and Uridine and Respectively Didanosine, Trimethoprim and Uridine Combinations Against K. pneumoniae EN0262 (Resistance Pattern ESBL (+)-(NP. +, MBL−, KPC+, CTX-M−, TEM+, OXA-1+) in Comparison to MIC of Several Commercial Antibiotics Table 21 shows the MIC values from Table 19 and 20 for FdUrd, trimethoprim and uridine and respectively didanosine, trimethoprim and uridine combinations against K. pneumoniae EN0262 (resistance pattern ESBL (+)->(NP. +, MBL −, KPC+, CTX-M −, TEM +, OXA-1 +) in comparison to MIC values of several commercial antibiotics.

| Antibiotic | MIC (μg/ml) |
|---|---|
| FdUrd; Trimethoprim; Uridine combination | 2; 4; 200 |
| Didanosine; Trimethoprim; Uridine combination | 2; 4; 200 |
| AMP, ampicillin | >128 |
| AMC, amoxicillin-clavulanic acid | >64 |
| PIP, piperacillin | >256 |
| TZP, piperacillin-tazobactam | 64 |
| CTX, cefotaxime | >32 |
| CAZ, ceftazidime | >32 |
| FEP, cefepime | >16 |
| ATM, aztreonam | >16 |
| IPM, imipenem | >4 |
| MEM, meropenem | >8 |
| GEN, gentamicin | 1 |
| AMK, amikacin | 8 |
| CIP, ciprofloxacin | >2 |
| SXT, trimethoprim-sulfamethoxazole | 4 |
| TET, tetracycline | 4 |
| TGC, tigecycline | 2 |
| CST, colistin | 1 |

MIC data for commercial antibiotics against K. pneumoniae EN0262 (resistance pattern ESBL (+) -> (NP.+, MBL−, KPC+, CTX-M−, TEM+, OXA-1+) were provided by IMBIM, BMC, Uppsala University, Uppsala, Sweden.

Example 22: Effects of AZT Combined with Trimethoprim and Uridine and Effect of FdUrd Combined with Trimethoprim and Uridine Against Salmonella and Heliobacter The effects of AZT combined with trimethoprim and uridine are shown in Table 22A and the resistance patterns of the Salmonella strains in Table 22B. It is evident that the AZT+trimethoprim+uridine combination inhibits strains of Salmonella resistant also to trimethoprim-sulfa. Inhibition of Heliobacter is important in view of increasing resistance and its association to gastric cancer.

TABLE 22A

| Pathogen | AZT (µg/ml) | Trimethoprim (µg/ml) | MIC (µg/ml) Uridine (µg/ml) | FdUrd (µg/ml) | Trimethoprim (µg/ml) | Uridine (µg/ml) |
|---|---|---|---|---|---|---|
| S. flexneri APV00906 | 1 | 1 | 100 | >4 | >8 | >400 |
| S. flexneri APV00907 | 2 | 2 | 200 | >4 | >8 | >400 |
| S. sonnei APV00908 | 0.03 | 0.03 | 3 | >4 | >8 | >400 |
| Helicobacter pylori APV00918 | 0.06 | 0.06 | 6 | 0.06 | 0.125 | 6 |
| Helicobacter pylori ATTC43504 | 0.125 | 0.125 | 13 | 0.06 | 0.125 | 6 |

TABLE 22B

| Antibiogram MIC (µg/ml) | S. flexneri APV00906 | S. flexneri APV00907 | S. sonnei APV00908 |
|---|---|---|---|
| Amoxi/Clav | S 4 | I 16 | S ≤ 2 |
| Piper/tazo | S ≤ 4 | S ≤ 4 | S ≤ 4 |
| Cefotaxime | S ≥ 64 | S ≤ 1 | S ≤ 1 |
| Ceftazidime | I 16 | S ≤ 1 | S ≤ 1 |
| Cefrtriaxon | / | S | S |
| Cefepime | S 2 | S ≤ 1 | S ≤ 1 |
| Ertapenem | S ≤ 0.5 | S ≤ 0.5 | S ≤ 0.5 |
| Imipenem | S ≤ 0.25 | S ≤ 0.25 | S ≤ 0.25 |
| Meropenem | S ≤ 0.25 | S ≤ 0.25 | S ≤ 0.25 |
| Amikacin | R* 16 | R* 4 | R* 4 |
| Gentamicin | R* 4 | R* ≤1 | R* ≤1 |
| Ciproflaxin | S ≤ 0.25 | S ≤ 0.5 | S ≤ 0.5 |
| Tigeciclin | S ≤ 0.5 | S ≤ 0.5 | S ≤ 0.5 |
| Nitrofurantoin | S ≤ 16 | S ≤ 16 | S ≤ 16 |
| Trimet/sulfmeto | R ≥ 320 | R ≥ 320 | R ≥ 160 |

Example 23: In Vivo Effect of AZT Combined with Trimethoprim and Uridine

This combination and AZT and trimethoprim separately were given to mice infected with *E. coli*. A murine peritonitis model was run, and the result is shown in Table 23B below. A potent inhibition was observed by the combination. A slight inhibition was obtained by dosing AZT and trimethoprim separately. Mice have been reported to have higher plasma concentrations of thymidine than humans. Table 23A shows the in vitro sensitivity of the *E. coli* strain used.

TABLE 23A

| Plate | MIC against *E. coli* ATCC 25922 |
|---|---|
| A | 0.06 µg/ml AZT + 0.06 µg/ml TMP with 50 µg/ml uridine |
| B | 0.5 µg/ml AZT |
| C | 0.5 µg/ml TMP |
| D | 0.5 µg/ml AZT + 0.5 µg/ml TMP with 50 µg/ml uridine and 2 µg/ml thymidine |
| E | >2 µg/ml AZT with 2 µg/ml thymidine |
| F | 1 µg/ml TMP with 2 µg/ml thymidine |

TABLE 23B

| Treatment | mouse no. | score at sampling | CFU/ml PF | log CFU/ml PF | mean log peritoneum | log diff peritoneum vs start of treatment |
|---|---|---|---|---|---|---|
| None | 1 | 1 | 1.48E+05 | 5.17 | 5.30 | |
|  | 2 | 1 | 1.45E+05 | 5.16 | | |
|  | 3 | 1 | 1.68E+05 | 5.23 | | |
|  | 4 | 1 | 4.50E+05 | 5.65 | | |
| Trimethoprim 30 mg/kg | 5 | 1 | 9.50E+03 | 3.98 | 5.34 | 0.04 |
|  | 6 | 1 | 1.60E+06 | 6.20 | | |
|  | 7 | 1 | 3.25E+05 | 5.51 | | |
|  | 8 | 1 | 4.75E+05 | 5.68 | | |
| AZT 30 mg/kg | 9 | 1 | 1.65E+04 | 4.22 | 5.68 | 0.38 |
|  | 10 | 1 | 4.25E+05 | 5.63 | | |
|  | 11 | 1 | 1.10E+07 | 7.04 | | |
|  | 12 | 1 | 6.75E+05 | 5.83 | | |
| AZT + TMP + uridine 30-30-50 | 13 | 1 | 8.75E+03 | 3.94 | 3.58 | −1.72 |
|  | 14 | 1 | 8.75E+03 | 3.94 | | |
|  | 15 | 1 | 5.50E+03 | 3.74 | | |
|  | 16 | 1 | 5.00E+02 | 2.70 | | |
| AZT + TMP + uridine 10-10-50 | 17 | 0 | 4.25E+03 | 3.63 | 3.45 | −1.85 |
|  | 18 | 0 | 4.25E+03 | 3.63 | | |
|  | 19 | 0 | 1.75E+03 | 3.24 | | |
|  | 20 | 0 | 2.00E+03 | 3.30 | | |
| AZT + TMP + uridine 3-3-50 | 21 | 1 | 1.13E+04 | 4.05 | 4.65 | −0.65 |
|  | 22 | 1 | 1.05E+04 | 4.02 | | |
|  | 23 | 1 | 3.25E+04 | 4.51 | | |
|  | 24 | 1 | 1.00E+06 | 6.00 | | |

TABLE 23B-continued

| Treatment | mouse no. | score at sampling | CFU/ml PF | log CFU/ml PF | mean log peritoneum | log diff peritoneum vs start of treatment |
|---|---|---|---|---|---|---|
| AZT + TMP + uridine 1-1-50 | 25 | 1 | 3.25E+05 | 5.51 | 5.79 | 0.49 |
| | 26 | 2 | 5.00E+04 | 4.70 | | |
| | 27 | 2 | 1.03E+07 | 7.01 | | |
| | 28 | 2 | 8.25E+05 | 5.92 | | |
| Ciprofloxacin 14 mg/kg | 29 | 0 | 1.75E+03 | 3.24 | 2.91 | −2.39 |
| | 30 | 0 | 2.50E+02 | 2.40 | | |
| | 31 | 0 | 1.00E+03 | 3.00 | | |
| | 32 | 0 | 1.00E+03 | 3.00 | | |
| Vehicle | 33 | 1 | 7.00E+07 | 7.85 | 7.36 | 2.06 |
| | 34 | 1 | 1.58E+06 | 6.20 | | |
| | 35 | 1 | 6.25E+07 | 7.80 | | |
| | 36 | 1 | 7.75E+07 | 7.89 | | |
| | 37 | 1 | 1.18E+07 | 7.07 | | |

Example 24: Triple Combinations with Sulfadiazine and Sulfamethoxazole Against *E. coli*

Table 24A and 24B shows the MIC values (μg/ml) of AZT against *E. coli* strain 2 in the presence of varying concentrations of uridine (μg/ml) as well as trimethoprim and sulfamethoxazole mixed in ratios of 0.25:1.25 μg/ml.

TABLE 24A

| Uridine (μg/ml) | MIC AZT (μg/ml) Sulfadiazine 1.25 μg/ml Trimethoprim 0.25 μg/ml |
|---|---|
| 0 | >0.5 ≤ 1 |
| 10 | >0.5 ≤ 1 |
| 100 | >0.25 ≤ 0.5 |

TABLE 24B

| Uridine (μg/ml) | MIC AZT (μg/ml) Sulfamethoxazol 1.25 μg/ml Trimethoprim 0.25 μg/ml |
|---|---|
| 0 | >0.5 ≤ 1 |
| 10 | >0.05 ≤ 1 |
| 100 | ≤0.05 |

The invention claimed is:

1. A method of enhancing the antibacterial effect in a subject of at least one nucleoside analogue, which method comprises administering an effective amount of said at least one nucleoside analogue to a subject in need thereof in combination with at least one second compound selected from the group consisting of uridine, cytidine and prodrugs thereof; and at least one third compound which is a tetrahydrofolate synthesis inhibitor; wherein said nucleoside analogue is selected from the group consisting of AZT, FdUrd, gemcitabine,didanosine, 5-fluorouracil, 5-bromouracil, 5-iodouracil (IdUrd), FLT, flucytosine, 5-bromouridine (BrUrd), stavudine, telbivudine, entecavir, emtricitabine, adefovir, lamivudine, tenofovir, vidarabine, abacavir, cytarabine, aracytidine, cidofovir, zalcitabine, ribavirin, idoxuridine, trifluoruridine, mercaptopurine, 5-ethyldeoxyuridine, thioguanine, 5-chlorodeoxyuridine, pentostatin, cladribine, clofarabine, fludarabine, nalarabine, allopurinol, FMdc, sinefungin, troxacitabine, vidaza, nelarabine, decitabine, CNDAC, ECyd, sofosbuvir, sapacitabine, mericitabine, amdoxovir, apricitabine, telbivudine, clevudine, bestifovir, brincidofovir, nicavir, and prodrugs thereof.

2. A method according to claim 1, wherein the tetrahydrofolate synthesis inhibitor is a trimethoprim compound.

3. A method according to claim 1, wherein the toxicity of the nucleoside analogue(s) is reduced by the second compound which also enhances the antibacterial effect.

4. A method according to claim 1, wherein the combined antibacterial effect of the nucleoside analogue and the second and third compound is greater than the sum of the effect provided if administered separately and the toxicity reduced.

5. A method according to claim 1, wherein the nucleoside analogue(s) is selected from the group consisting of AZT; FdUrd;5-fluorouracil; BrdUrd; IdUrd; didanosine and gemcitabine.

6. A method according to claim 5, wherein the nucleoside analogue is AZT, the second compound is uridine and the third compound is trimethoprim.

7. A method according to claim 5, wherein the nucleoside analogue is FdUrd, the second compound is uridine and the third compound is trimethoprim.

8. A method according to claim 5, wherein the nucleoside analogue is didanosine, the second compound is uridine and the third compound is trimethoprim.

9. A method according to claim 5, wherein the nucleoside analogue is BrdUrd, the second compound is uridine and the third compound is trimethoprim.

10. A method according to claim 1, wherein the subject is a mammal.

11. A composition comprising as a first compound at least one nucleoside analogue which is capable of decreasing a bacterial colonisation or infection of a subject; a second compound which is capable of decreasing mitochondrial toxicity of said nucleoside analogue(s) while at the same time increases its antibacterial effect; and a third compound capable of decreasing the concentration in bacteria of nucleosides and/or nucleotides known to compete with nucleoside analogues; wherein said nucleoside analogue is selected from the group consisting of AZT, FdUrd, gemcitabine, didanosine, 5-fluorouracil, 5-bromouracil, 5-iodouracil (IdUrd), FLT, flucytosine, 5-bromouridine (BrUrd), stavudine, telbivudine, entecavir, emtricitabine, adefovir, lamivudine, tenofovir, vidarabine, abacavir, cytarabine, aracytidine, cidofovir, zalcitabine, ribavirin, idoxuridine, trifluoruridine, mercaptopurine, 5-ethyldeoxyuridine, thioguanine, 5-chlorodeoxyuridine, pentostatin, cladribine, clofarabine, fludarabine, nalarabine, allopurinol, FMdc, sinefungin, troxacitabine, vidaza, nelarabine, decitabine, CNDAC, ECyd, sofosbuvir, sapacitabine, mericitabine, amdoxovir, apricitabine, telbivudine, clevudine, bestifovir, brincidofovir, nicavir, and prodrugs thereof; wherein said second compound is selected from the group consisting of uridine, cytidine and prodrugs thereof; and wherein said third compound is a tetrahydrofolate synthesis inhibitor.

12. A composition according to claim 11, wherein the first compound is selected from the group consisting of AZT, FdUrd, 5-fluorouracil, BrdUrd, IdUrd, didanosine, gemcitabine and prodrugs giving rise to these compounds.

13. A composition according to claim 11, wherein the second compound is a compound selected from the group consisting of uridine, and prodrugs giving rise to uridine.

14. A composition according to claim 11, in combination with a carrier suitable for use in a medicament.

15. A pharmaceutical preparation comprising at least one first compound selected from the group consisting of AZT, FdUrd, 5-fluorouracil, BrdUrd, IdUrd, didanosine and gemcitabine; at least one second compound selected from the group consisting of uridine and prodrugs giving rise to uridine; and at least one third compound which is a tetrahydrofolate synthesis inhibitor; or a pharmaceutically acceptable salt thereof, together with a pharmaceutically acceptable carrier.

16. A pharmaceutical preparation according to claim 15, wherein the first compound is AZT, the second compound is uridine and the third compound is trimethoprim.

17. A pharmaceutical preparation according to claim 15, which is in liquid form.

18. A pharmaceutical preparation according to claim 15, which is in a solid form suitable for oral administration.

19. A method of treating or preventing a bacterial infection or colonisation in a subject, which method comprises administering a therapeutically efficient amount of at least one first compound selected from the group consisting of AZT, FdUrd, 5-fluourouracil, BrdUrd, IdUrd, didanosine and gemcitabine;

at least one second compound selected from the group consisting of uridine and prodrugs giving rise to uridine; and at least one third compound which is a tetrahydrofolate synthesis inhibitor to said subject.

20. The method according to claim 19, wherein at least one compound selected from the group consisting of uridine and prodrugs giving rise to uridine is co-administered with the at least one first compound and trimethoprim and/or trimethoprim compound(s).

21. The method according to claim 19, wherein the bacterial infection or colonization is due to Gram-negative or Gram-positive bacteria selected from the group consisting of *Acinetobacter; Bacillus; Bordetella; Campylobacter; Citrobacter; Clostridium; Corynebacteria; Enterobacter; Escherichia; Haemophilus; Heliobacter; Klebsiella; Legionella; Listeria; Micrococcus; Moraxella; Mycobacteria; Neisseria; Proteus; Pseudomonas; Salmonella; Shigella; Staphylococcus; Streptococcus; Vibrio* and *Yersinia*.

22. A method according to claim 21, wherein the subject is a mammal, and the method provides an enhanced potency of the at least one first compound as well as a decreased toxicity to the subject as compared to the result of separate administration of said compounds.

23. The method according to claim 2, wherein the trimethoprim compound is trimethoprim-sulfa.

24. The method according to claim 1, wherein the nucleoside analogue is selected from the group consisting of AZT, FdUrd, and didanosine.

* * * * *